United States Patent [19]

Leighton et al.

[11] Patent Number: 5,262,128
[45] Date of Patent: Nov. 16, 1993

[54] ARRAY-TYPE MULTIPLE CELL INJECTOR

[75] Inventors: Stephen B. Leighton, Maplewood, N.J.; Michael J. Brownstein, Rockville, Md.

[73] Assignee: The United States of America as represented by the Department of Health and Human Services, Washington, D.C.

[21] Appl. No.: 425,254

[22] Filed: Oct. 23, 1989

[51] Int. Cl.⁵ .............................................. C12M 1/26
[52] U.S. Cl. .................................. 422/100; 422/102; 435/287; 435/293; 435/294; 435/301; 436/63; 436/165; 436/180; 436/809
[58] Field of Search ............... 422/100, 102; 436/180, 436/165, 63, 809; 435/293, 294, 301, 287; 73/863.31, 864.72; 935/53, 85

[56] References Cited

U.S. PATENT DOCUMENTS

| | | | |
|---|---|---|---|
| 4,158,035 | 6/1979 | Haase et al. | 422/100 |
| 4,162,896 | 7/1979 | Hosli | 422/100 X |
| 4,276,048 | 6/1981 | Leaback | 436/180 |
| 4,461,328 | 7/1984 | Kenney | 141/67 |
| 4,478,094 | 10/1984 | Salomaa et al. | 73/863.32 |
| 4,599,315 | 7/1986 | Terasaki et al. | 436/180 X |
| 4,619,899 | 10/1986 | Nikitin et al. | 435/287 |
| 4,664,097 | 5/1987 | McGrath et al. | 128/1 R |
| 4,695,547 | 9/1987 | Hilliard et al. | 435/173 |

OTHER PUBLICATIONS

"Fabrication of Microstructures Using the Liga Process", by W. Ehrfeld, et al., Proceedings of the IEEE Micro-Robots and Teleoperators Workshop, Hyannis, Mass., 1987, IEEE Catalog No. 87TH0204-8.

Primary Examiner—James C. Housel
Assistant Examiner—Ramon Torres
Attorney, Agent, or Firm—Lowe, Price, LeBlanc & Becker

[57] ABSTRACT

An injection device injects small amounts of injectate into each of a plurality of cells. A first plate, which may be made from a silicon chip, includes a large number of evenly spaced cell wells, in a regular array. Each well includes a through hole in the chip. A top plate, also formed from a silicon chip, includes a plurality of injection needles, arranged in a regular array corresponding to the position of the cell wells. A suspension of cells is washed over the first plate and individual cells are retained by the individual wells. A vacuum may be applied to the cell wells through a manifold beneath the first plate, thus to retain the cells in place. Excess cells and suspension are removed by washing the plate. The second plate, including the injection needles, is positioned on the first plate so that the needles pierce the plurality of cells retained in the wells, thus simultaneously introducing the injectate into a large number of individual cells.

27 Claims, 2 Drawing Sheets

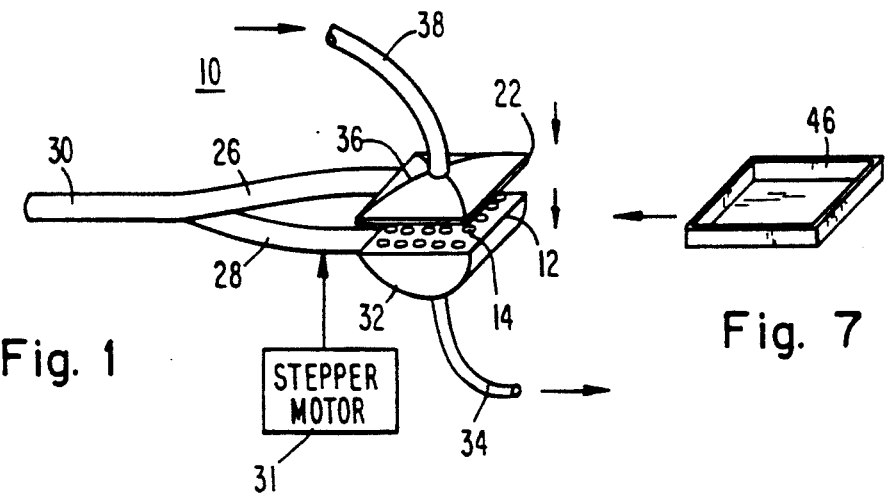
Fig. 1
Fig. 7
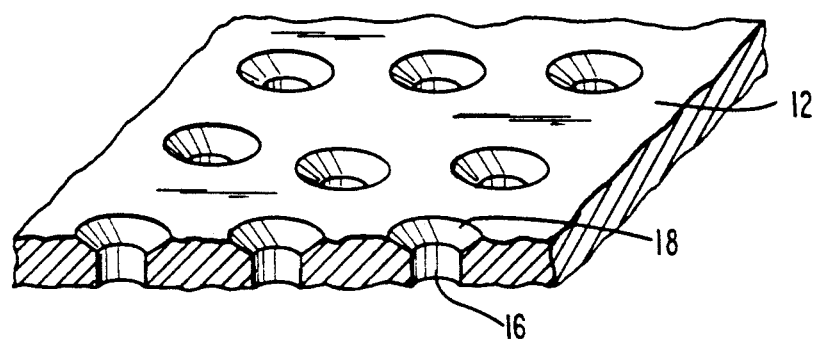
Fig. 2
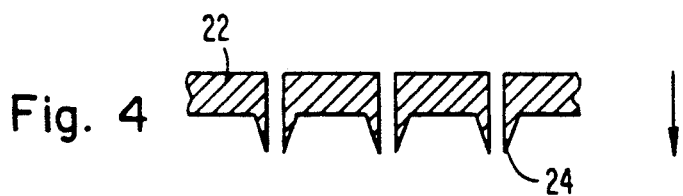
Fig. 4
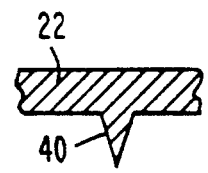
Fig. 5
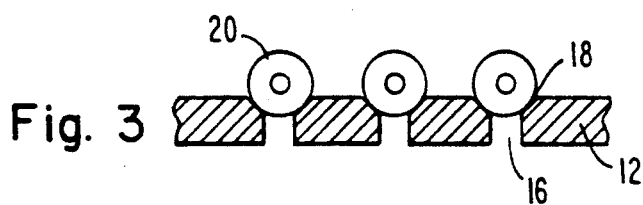
Fig. 3
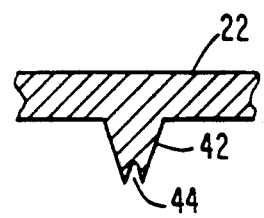
Fig. 6

ARRAY-TYPE MULTIPLE CELL INJECTOR

TECHNICAL FIELD

This invention relates to injection devices, and more particularly to structures for substantially simultaneous injection of a medium into a plurality of individual cells.

BACKGROUND ART

In modern biotechnological operations, it is often necessary to inject small amounts of protein, DNA, RNA, drugs or other substances into each of a plurality of living cells. For example, quantities such as 20 to 50 nanoliters may be desired to be injected into each of a plurality of frog oocytes. Alternatively, a few nanoliters (1 to 10) may be required to be injected in mouse stem cells. These injections are frequently required to be made quickly and easily into large numbers of cells, for example, into thousands or tens of thousands of cells.

Such injection is presently carried out manually, utilizing micromanipulators to hold micropipettes, and further utilizing a microscope for visual observation. Some mechanization has been developed for such techniques. One device is available under the designation Stoelting Model 567-57-RH. Another is available under the designation Narishigi Model MO203. However, even with such devices, significant manual intervention is required. For example, in one known device, the cells are plated on a cover slip or petri dish. A computer controlled microscope having a TV camera is manipulated by an operator. A joy stick is used to manipulate the device until a cell is observed under a cross hair. The computer is given information to execute an injection program. However, such devices are expensive, do not create regular distributions of cells, operate slowly, and can only inject approximately 2,000 cells per hour. Thus, such devices cannot easily and inexpensively perform injections of tens of thousands of cells.

Moreover, such prior art devices do not work for cells in a suspension but are limited only to cell types which adhere to surfaces. Moreover, requirement of a human operator to identify the location of each of the cells to be injected adds yet a further expense to operation of the devices.

Electroporation is another known technology for introducing molecules into cells. This technique suffers from at least two disadvantages relative to the present invention, however. First, in typical electroporation, the substance to be introduced must be dispersed throughout the suspension medium, thus requiring the use of much more injectant material. Second, electroporation does not introduce material into the nucleus of the cell.

Lyposomes or calcium phosphate precipitation can also be used to deliver certain materials into cells. However, their use is somewhat limited.

Accordingly, there is a need in the prior art for a device which enables a more rapid injection of large numbers of cells, which does not require tedious human intervention, which is inexpensive, which may be disposable, which is highly efficient in the use of injecting solution which may be quite precious, which introduces injected material into the cell nucleus, which does not require the use of any special biological, which can deliver practically any water-soluble material into the cells and is parsimonious in its use of the valuable reagents, and which is constructed entirely of inert, biocompatible materials.

DISCLOSURE OF THE INVENTION

It is accordingly an object of the present invention to overcome the deficiencies of the prior art and to provide apparatus for rapid injection of a medium into a large number of cells.

Still another object of the invention is the provision of the device for substantial simultaneous injection of large numbers of cells without requiring special operator skills.

It is yet a further object of the invention to provide an apparatus for parsimoniously injecting material into the nucleus or into the cytoplasm of each of a plurality of cells.

It is a more specific object of the invention to provide an apparatus for injecting a medium to a plurality of cells, including a first structure with a plurality of wells for holding the cells in a regular array, a second structure having a plurality of injection needles spaced in an array corresponding to the regular array of the cells, and a third structure for positioning the first and second structures accurately with respect to one another.

Preferably, each of the wells holds only a single cell.

The arrays used in the first and second structures may be linear or may be two-dimensional and more specifically rectangular. The wells may be cylindrical, with a counter-sunk conical upper section for guiding the cells thereto. Moreover, the wells may be in the form of through holes in a plate structure.

Preferably, the first and second structure may be formed on silicon chips utilizing micromachining techniques which are known in the art for fabrication of integrated circuits and the like. The wells may form through holes in the chip forming the first structure and a pressure generating means may be used to retain the cells in the wells by generating a pressure differential. A manifold chamber in sealing arrangement with the surface of the chip opposite to the surface facing the injection needles may be used for this purpose.

The injection needles may be solid or hollow. Hollow needles may include a cavity at a tip portion, or may include a through hole passing through the needles and the chip support therefor. In this embodiment of the invention, a manifold may be provided on the surface of the chip opposing the surface bearing the needles. The manifold is preferably in the form of a chamber for holding the medium to be injected. A pressure generating means may be used to pressurize the manifold in order to inject the medium through the needles into the cells.

The third structure for positioning the first and second structures is preferably arranged to provide perpendicular motion for the two structures relative to one another. Thus, for parallel chips formed to include the wells and the injection needles respectively, the third structure moves the chips perpendicularly towards and away from one another in order to provide contact between the plurality of injection needles and cells contained in each of the wells.

Such a structure may be a tweezer-like arrangement having a pair of arms extending from a flexible hinge. An electrically controlled device may be provided for generating the motion, which may include a stepper motor.

Alternatively, at least one of the structures bearing the needles and the wells may have a convex curvature relative to the other, in order to facilitate contact between the needles and the cells by a rolling motion of that structure relative to the other.

Other objects, features and advantages of the present invention will become readily apparent to those skilled in the art from the following description wherein there is shown and described a preferred embodiment of the invention, simply by way of illustration and not of limitation of the best mode (and alternative embodiments) for carrying out the invention. The invention itself is set forth in the claims appended hereto. As will be realized upon examination of the specification with due reference to the drawings, the present invention is capable of still other, different, embodiments and its several details are capable of modifications in various obvious aspects, all without departing from the invention which is recited in the claims. Accordingly, the drawings and the descriptions provided herein are to be regarded as illustrative in nature and not as restrictive of the invention.

BRIEF DESCRIPTION OF DRAWINGS

In accordance with the above described objects and features of the invention, a preferred embodiment thereof is shown in the accompanying drawings, wherein:

FIG. 1 is a prospective view of an embodiment of the invention;

FIG. 2 is a detailed section and prospective view of a cell retaining plate which may be used in the invention;

FIG. 3 is a sectional view of the cell retaining plate of FIG. 2 including a plurality of cells therein;

FIG. 4 is a detailed sectional view of a needle bearing plate for use in the invention;

FIG. 5 is a partial sectional view of an alternate embodiment of the needle plate of FIG. 4;

FIG. 6 is a partial sectional view of still another alternate embodiment of the needle bearing plate of FIG. 4;

FIG. 7 is a prospective view of a trough which may be used for temporary filling of a needle bearing plate incorporate needles of the type shown in type 6;

BEST MODE FOR CARRYING OUT THE INVENTION

Figure 8:
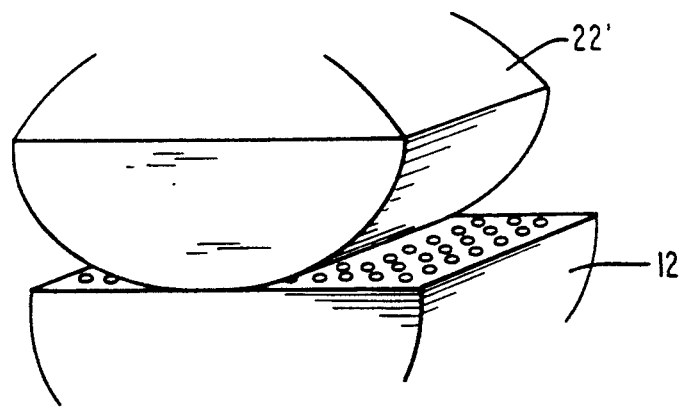
FIG. 8 shows a modification of the preferred embodiment of the invention.

Referring now to FIG. 1, there is illustrated at reference numeral 10 an apparatus according to the invention. As shown therein, a lower plate 12 includes a plurality of cell wells 14. Lower plate 12 retains the cells in wells 14, as would be appreciated upon reference to FIGS. 2 and 3. As illustrated therein, each of the cell wells includes a through hole 16 having a countersunk frustoconical upper section 18. When the individual cells to be injected are retained by plate 12, they are preferably seated within the frustoconical sections 18 as illustrated at FIG. 3. Thus, it is seen that in order to provide an ordered array of cells 20, the through holes 16 are of a smaller diameter than the diameter of the cells. Although the frustoconical upper sections of through holes 16 are shown in the embodiment of FIGS. 2 and 3 and provide improved seating of the cells, it will be appreciated by those skilled in the art that the frustoconical sections are not necessary and may be omitted.

An upper plate 22, shown in FIGS. 1 and 4, includes a plurality of injecting needles disposed in an array matching the array of cell wells on lower plate 12.

When lower and upper plates 12 and 22 are properly aligned, a needle 24 is provided opposite each through hole 16. Accordingly, when cells 20 are properly retained by plate 12 in the through holes 16, upper plate 22 may be lowered and, in a single movement, each of cells 20 will be injected with the injection medium via a corresponding needle 24.

In the preferred embodiment the plates are moved toward one another by a mechanical structure, including a pair of arms 26 and 28, flexibly connected at a flexible hinge 30. An electrically controlled device, such as a stepper motor 31 symbolically illustrated in FIG. 1, may be used to move the arms. Thus, the hinged structure including hinge 30 and arms 26 and 28, having a general tweezer-like appearance, is used to move the upper and lower plates, which are generally parallel to one another, in a perpendicular direction towards and away from one another in order to provide in a single movement an injection of a large number of cells.

As seen in FIG. 1, a manifold chamber 32 is disposed below plate 12. The chamber is connected by a pipe 34 to a pressure control device (not shown). A negative pressure may be provided to the manifold chamber 32 in order to attract each of cells 20 to the through holes 16. Thus, once the cells are seated on the frustoconical sections 18 (or directly on the through holes 16), application of a vacuum retains the cells in the appropriate locations for injection by needles 24 provided on plate 22.

In one embodiment of the invention, needles 24 provide through holes in upper plate 22. A second manifold chamber 36 is disposed above the plate 22. A second pipe 38 connects manifold chamber 36 to a fill, inject and rinse control device (not shown). Thus, the medium to be injected may be provided through pipe 38 to manifold chamber 36. Upon application of a positive pressure from the fill, inject and rinse control device, through pipe 38 to manifold chamber 36, the injection medium is provided under pressure by the through holes associated with needles 24 to each of the cells 20. Upon conclusion of the injection process, plates 22 and 12 are separated from one another. Cells 20 may be left on the lower plate 12 in an appropriate maintenance medium, or may be removed into suspension or onto an agar plate, for example, by releasing the vacuum applied to pipe 34 which previously retained the cells in place, and possibly by providing a positive pressure to manifold chamber 32. Upper plate 22 and lower plate 12 may be flushed, cleaned and reused, or may be disposed of.

Plates 12 and 22 may be constructed to have the structure illustrated in FIG. 2 on a microminiature scale, preferably by micromachining a silicon chip utilizing techniques well known in the integrated circuit industry. However, other techniques may be used to fabricate the plates, such as by using etchable glass, diamond grinding, or other techniques. Various techniques are described in an article entitled "Fabrication of Microstructures Using the Liga Process" by W. Ehrfeld, et al., published in the Proceedings of the IEEE Microrobots and Teleoperators Workshop held in Hyannis, Mass., November, 1987 and available from IEEE under catalogue 87 TH0204-8. It will be appreciated that cell wells 14 would be manufactured to have appropriate diameters for the size of the cells to be injected. Thus, when injecting a number of frog eggs having diameters of approximately 1 millimeter, the through holes would be provided with diameters of somewhat less than 1 millimeter and thus, on a 1 centimeter by 1 centimeter chip, approximately a 10 by 10 array of cell wells may be provided. Alternatively, when smaller cells are being injected, such as stem cells having diameters of approximately 10 microns, a 1 centimeter square plate may have an array of 10,000 cell wells arranged in a 100 by 100 array. Thus, with the aid of micromachining, any size array may be manufactured.

The inventive structure, unlike the prior art, will work with cells in a suspension. All cell types may be put into suspension, including those which naturally grow on surfaces. Thus, by placing a film of the suspension over the lower plate 12, the suspended cells are attracted into the wells upon application of suction to pipe 34. As will be appreciated, the structure of FIGS. 1-4 provides simultaneous injection of tens of thousands of cells, in a very short period of time, and is highly efficient in utilization of the injection medium which may be quite rare and/or expensive.

In the illustration of FIG. 3, the nuclei of the various cells are shown as being positioned substantially at the center of the through holes 16. Thus, for a cell population having uniform diameters and nuclei positions, the inventive structure may be utilized to introduce material into the cell nuclei. The invention thus provides an advantage over the known electroporation technique, which does not introduce material into the nucleus. Of course, the present invention could be utilized in combination with electroporation equipment. However, the material is nonetheless provided by injection into the plural cells.

The manifold chamber 32, sealed to the underside of the chip forming lower plate 12, covers all of the small through holes 16 to permit both positive and negative pressure to be applied thereto. Manifold chamber 32 is connected by pipe 34 to a pressure control device acting as a source of vacuum or positive pressure. A pump, a syringe or a regulator may be used to provide the varying pressure. The applied pressure, whether positive or negative, may be in the range of 0 to 15 psi. Typically, the applied pressure differential is sufficient to hold the cells in place for the injection procedure, without permitting the cells to be displaced by buoyancy thereof, by a tendency to sink or due to a stirring operation. However, the pressure differential is not so high as to rupture the cell wall by extruding the wall into the well holes in the array. Although a wide pressure range (0 to 15 inches of water) is contemplated, a low pressure may be sufficient for retaining frog oocytes, while a greater pressure may be required for retaining smaller cells in the wells. Moreover, although the cell wells are shown as being circular in shape, it would be clear to those of ordinary skill in the art that other shapes may be used, such as square, elliptical, etc.

Upon placing the inventive apparatus 10 in a suspension of cells, or by pouring or flowing such a suspension over the array of recesses, the cells are provided between the lower and upper plates. Upon application of suction to manifold chamber 32, a "filtering" process is begun wherein suspension liquid flows through the holes in the chip forming lower plate 12 until, eventually, most or all of the cell wells become filled with cells which cannot pass therethrough but which, instead, nest in the recesses, being retained at least in part by the pressure differential between the two sides of the plate 12. Excessive cells which may accumulate along plate 12 but which are not contained in the cell wells, as well as surplus cell suspension fluid, may be removed by a gentle cross-flushing while the cell wells each continue to contain a cell by the above-noted differential pressure applied thereto.

Figure 9:
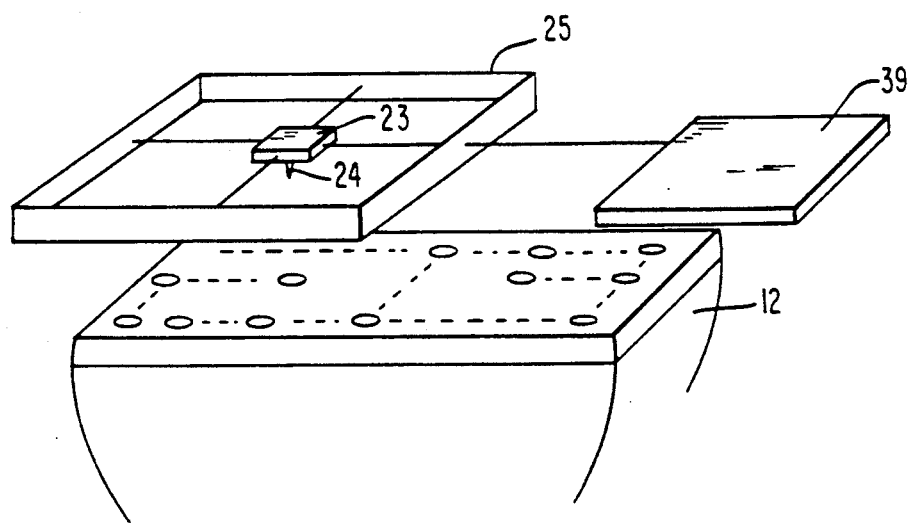
FIG. 9 shows yet another embodiment wherein a single injection needle is movable among the individual cell wells.
Figure 10:
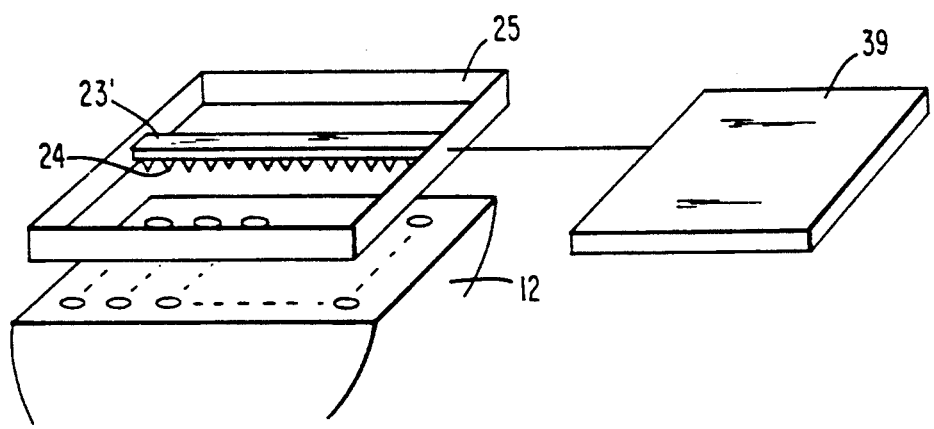
FIG. 10 shows still another embodiment of the invention wherein a linear array of injection needles is movable among the individual cell wells.

It is noted that although the inventive structure is illustrated as providing a plurality of needles 24 on upper plate 22, injection may, in fact, proceed by positioning a micropipette in turn over each cell well to provide automatic penetration and injection by a programmed mechanical actuator as previously described. However, while in the prior art the cells are provided in random arrays on a cover slip or petri dish, an arrangement which requires significant expenditures of time to locate the individual cells, the inventive structure provides a regular array of cells. Thus, positioning of the mechanical injection actuator may be programmed into a known numerically controlled machine tool. Accordingly, utilization of a structure incorporating only the lower plate 12 in conjunction with existing mechanical injection actuators provides significant increases in the number of cells which may be injected. Such an arrangement is shown in the partial view of FIG. 9, wherein an injection actuator 23 includes an arrangement of a pipette and a single injection needle 24 in a modified upper plate structure 25. A positioning device 39, such as a numerically controlled machine tool, is used to position the injection actuator 23 relative to the cell wells in the lower plate 12. FIG. 10 shows a further modification of the inventive concept, wherein the injection needles are arranged in a linear array, as hereinabove mentioned. Thus, a modified injection actuator 23' is shown as including the linear array of injection needles in a frame of the modified upper plate structure. The numerically controlled machine tool 39 may thus be required to move the array of needles in actuator 23' shown in FIG. 10 in only one direction, or may move a smaller number of needles in actuator 23 of FIG. 9 in two dimensions.

In order to increase the number of cells being injected still further, the invention incorporates both the lower and upper plates 12 and 22, respectively, as above noted. Such a device may have a cost of five dollars in comparison to a cost of $80,000 for existing programmed mechanical injection actuators. Moreover, the inventive device may inject 10,000 cells simultaneously while the mechanical actuators are capable of injecting 2,000 cells per hour.

Accordingly, the advantageous structure of FIG. 1 includes significant improvements over presently available devices for injection of large numbers of cells.

The upper plate 22 may be fabricated by etching away material of a silicon chip to leave behind projecting needles having the through holes. However, different injection needle structures may be utilized, as shown in FIGS. 5 and 6. Specifically, FIG. 5 illustrates a "poison dart" type of needle shown at 40, wherein a solid sharp projection extends from the surface of upper plate 22 toward a cell well of lower plate 12. In a third embodiment, shown at FIG. 6, the injection needle may be as shown at 42, including a cavity 44 at a tip portion thereof. It will be appreciated that the embodiment of FIG. 5 would be the simplest form to manufacture. Both the embodiments of FIG. 5 and 6, however, require the use of a shallow trough 46, shown in FIG. 7, for the medium to be injected. To perform the multiple cell injections in accordance with a structure utilizing the embodiments of FIGS. 5 or 6, the upper plate 22 is dipped in the trough 46. Capillary action causes the medium to fill the blind hole formed by cavity 44 in the embodiment of FIG. 6. For the embodiment of FIG. 5, a small amount of the injected material will adhere to the surface of needle 40. Upon removal of trough 46, the upper and lower plates are brought together, similarly to operation of the embodiment including the upper plate shown in FIG. 4. Each needle penetrates a corresponding cell and the medium then diffuses into the cell.

A modification of the preferred embodiment of FIG. 1 is shown in FIG. 8, wherein one of the two structures bearing the needles and the wells, illustratively shown as the upper plate 22' bearing the needles, is provided with a convex curvature relative to the other (lower plate 12). This modification facilitates contact between the needles and the cells by a rolling motion of the upper plate 22' relative to the lower plate 12.

In still another modification, electroporation potentials and/or iontophoresis may be used to transfer the injectate into the cells, since the required small volume of injectate has been efficiently positioned for each cell. It will be appreciated that the amount of injectate provided by a needle shown in the embodiment of FIG. 6 is more strictly and more easily controlled by the size of the cavity 44, thus avoiding waste of precious injectates.

The two dimensional array for holding larger cells, such as frog oocytes, may be formed of a nylon mesh, or woven net, such as Nylatek. Further, in order to cause the nuclei all to move toward the surface of the cells, a centrifugal force may be applied perpendicularly to the net. When the cells are thus aligned, injection of the nuclei is made simpler.

The foregoing description of the preferred embodiment of the invention has been presented for purposes of illustration and description and is not intended to be exhaustive or to limit the invention to the precise forms disclosed, since many modifications and variations are possible in light of the above teaching. The embodiment was chosen and described in order best to explain the principles of the invention and its practical application, thereby to enable others skilled in the art best to utilize the invention in various embodiments and with various modifications as are suited to the particular use contemplated therefor. It is intended that the scope of the invention be defined by the claims appended hereto, when interpreted in accordance with full breadth to which they are legally and equitably entitled.

We claim:

1. Apparatus for injection of a medium into a plurality of cells, comprising:
   first means having a plurality of cell wells arranged in a regular array for holding a plurality of individual cells in a regular array;
   second means having a plurality of injection needles spaced in an array corresponding to said regular array of said cell wells for injecting the medium into the individual cells; and
   third means for positioning said first and second means accurately with respect to one another.

2. Apparatus for injection of a medium into a plurality of cells as recited in claim 1, wherein said regular array is a linear array.

3. Apparatus for injection of a medium into a plurality of cells, comprising:
   first means having a plurality of cell wells arranged in a regular array for holding a plurality of cells in a regular array;
   second means having a plurality of injection needles spaced in an array corresponding to said regular array of said cell wells; and
   third means for positioning said first and second means accurately with respect to one another, wherein
   each of said wells has a predetermined size selected to match a size of a single cell, thereby limiting each well to hold therein only one cell.

4. Apparatus for injection of a medium into a plurality of cells as recited in claim 3, wherein said regular array is a two-dimensional array.

5. Apparatus for injection of a medium into a plurality of cells as recited in claim 2, wherein said wells are cylindrical.

6. Apparatus for injection of a medium into a plurality of cells as recited in claim 5, wherein said wells include a counter-sunk conical upper section.

7. Apparatus for injection of a medium into a plurality of cells as recited in claim 1, wherein said first means comprises a chip and said wells comprise through holes having openings on opposing surfaces of said chip.

8. Apparatus for injection of a medium into a plurality of cells as recited in claim 7, further comprising pressure means for providing a pressure differential to retain the cells in said wells.

9. Apparatus for injection of a medium into a plurality of cells as recited in claim 8, wherein said pressure means comprises a manifold chamber in sealing engagement with one surface of said chip and wherein said second means is positioned on the opposite surface of said chip.

10. Apparatus for injection of a medium into a plurality of cells as recited in claim 1, wherein said injection needles are substantially solid.

11. Apparatus for injection of a medium into a plurality of cells as recited in claim 1, wherein said injection needles each comprise a hollow portion.

12. Apparatus for injection of a medium into a plurality of cells as recited in claim 11, wherein said hollow portion of said injection needles includes a cavity at a tip portion thereof contacting one of the cells.

13. Apparatus for injection of a medium into a plurality of cells as recited in claim 11, wherein said second means comprises a chip and said injection needles project from one surface thereof to said first means, each of said needles including a through hole passing therethrough and through said chip.

14. Apparatus for injection of a medium into a plurality of cells as recited in claim 13, further comprising a manifold on a surface of said chip opposite to said one surface, said manifold holding the medium to be injected by said needles.

15. Apparatus for injection of a medium into a plurality of cells as recited in claim 14, further comprising pressure means for pressurizing said manifold to inject the medium.

16. Apparatus for injection of a medium into a plurality of cells as recited in claim 1, wherein said first and second means each comprises a substantially planar chip, said planar chips arranged substantially parallel to one another, and said third means comprises means for moving said planar chips towards and away from one another, to provide contact between each injection needle and a cell in each said well.

17. Apparatus for injection of a medium into a plurality of cells, comprising:
   first means having a plurality of cell wells arranged in a regular array for holding a plurality of individual cells in a regular array;
   second means having a plurality of injection needles spaced in an array corresponding to said regular array of said cell wells for injecting the medium into the individual cells;
   third means for positioning said first and second means accurately with respect to one another;
   said first and second means each comprising a substantially planar chip, said planar chips arranged substantially parallel to one another, and said third means comprising means for moving said planar chips towards and away from one another, to provide contact between each injection needle and a cell in each said well, wherein
   said means for moving comprises a flexibly hinged structure having a pair of arms in a tweezer-like arrangement.

18. Apparatus for injection of a medium into a plurality of cells as recited in claim 17, wherein said means for moving comprises electrically controlled motion generating means.

19. Apparatus for injection of a medium into a plurality of cells as recited in claim 18, wherein said electrically controlled motion generating means comprises a stepper motor.

20. Apparatus for injection of a medium into a plurality of cells, comprising:
   first means having a plurality of cell wells arranged in a regular array for holding a plurality of individual cells in a regular array;
   second means having a plurality of injection needles spaced in an array corresponding to said regular array of said cell wells for injecting the medium into the individual cells; and
   third means for positioning said first and second means accurately with respect to one another, wherein
   said first and second means each comprises a plate, at least one of said plates having a convex curvature towards the other, thereby to facilitate contact between said needles and cells in said wells by a rolling motion of one plate relative to the other.

21. Apparatus for injection of a medium into a plurality of cells, comprising:
   first means having a plurality of cell wells for holding a plurality of cells in a regular array;
   second means having an injection needle; and
   third means for positioning said first and second means accurately with respect to one another for injecting the medium into each of the cells in the array.

22. Apparatus for injection of a medium into a plurality of cells as recited in claim 21, wherein each of said cell wells has a predetermined size selected to match a size of a single cell, thereby limiting each well to accept only a single cell therein, and said second means comprises a plurality of injection needles corresponding to the plurality of cell wells for individually injecting the medium into each single cell.

23. Apparatus for injection of a medium into a plurality of cells, comprising:
   first means having a plurality of cell wells positioned in a regular array for holding a plurality of individual cells, each cell well having a size selected to match a size of a single cell,
   second means having at least one injection needle spaced apart from said regular array of said cell wells for injecting the medium into an individual cell in one of said regular array of cell wells; and
   third means for successively positioning said first and second means with respect to one another to position said at least one injection needle in successive positions corresponding to said regular array of cell wells for successively individually injecting each of the cells.

24. Apparatus for injection of a medium into a plurality of cells as recited in claim 23, wherein said second means comprises only a single injection needle and said third means moves said single injection needle to individual positions respectively corresponding to the positions of individual ones of said plurality of cell wells in said regular array for individually injecting the single cells in said regular array of cell wells.

25. Apparatus for injection of a medium into a plurality of cells as recited in claim 23, wherein said second means comprises a plurality of injection needles arranged in a linear array for injecting the medium into each of a linear array of single cells.

26. Apparatus for injection of a medium into a plurality of cells as recited in claim 21, wherein:
   each cell well in said first means has a predetermined size selected to match a size of a single cell, thereby limiting each well to accept only a single cell therein,
   said second means comprises only a single injection needle and
   said third means moves said single injection needle to individual positions respectively corresponding to the positions of individual ones of said plurality of cell wells in said regular array for individually injecting the single cells in said regular array of cell wells.

27. Apparatus for injection of a medium into a plurality of cells as recited in claim 21, wherein:
   each cell well in said first means has a predetermined size with a diameter less than approximately 1 mm and selected to match a size of a single cell, thereby limiting each well to accept only a single cell therein, and
   said second means comprises a plurality of injection needles arranged in a linear array for injecting the medium into each of a linear array of single cells.

* * * * *